（12）United States Patent
Arumugam et al.

(10) Patent No.: US 12,117,851 B2
(45) Date of Patent: Oct. 15, 2024

(54) OXYGEN PRESSURE REGULATING DEVICE AND SYSTEM

(71) Applicant: QTRACK HEALTH SYSTEMS PRIVATE LIMITED, Chennai (IN)

(72) Inventors: M. Arumugam, Chennai (IN); P. R. Venkatesh, Chennai (IN)

(73) Assignee: QTRACK HEALTH SYSTEMS PRIVATE LIMITED, Chennai (IN)

( * ) Notice: Subject to any disclaimer, the term of this patent is extended or adjusted under 35 U.S.C. 154(b) by 0 days.

(21) Appl. No.: 17/874,123

(22) Filed: Jul. 26, 2022

(65) Prior Publication Data

US 2023/0066257 A1 Mar. 2, 2023

(30) Foreign Application Priority Data

Jul. 27, 2021 (IN) ............................. 202141033640

(51) Int. Cl.
*G05D 16/06* (2006.01)
(52) U.S. Cl.
CPC ................ *G05D 16/0625* (2013.01)
(58) Field of Classification Search
CPC ...... G05D 16/0625; A61M 2202/0208; A61M 16/201; A61M 16/1005; A61M 2205/3344; A61M 2205/70; A61M 2206/11
See application file for complete search history.

(56) References Cited

U.S. PATENT DOCUMENTS

| 2,301,031 | A | * | 11/1942 | Ferguson | ........... G05D 16/0619 |
| | | | | | 137/505.3 |
| 2,885,173 | A | * | 5/1959 | Dobrick | ................. B64D 13/02 |
| | | | | | 251/61.3 |
| 3,809,111 | A | * | 5/1974 | Olsson | .................... F16K 17/04 |
| | | | | | 137/503 |
| 2015/0322910 | A1 | * | 11/2015 | Snodgrass | ............... F02C 7/232 |
| | | | | | 137/12 |

* cited by examiner

*Primary Examiner* — Patrick C Williams
(74) *Attorney, Agent, or Firm* — Klarquist Sparkman, LLP

(57) ABSTRACT

An oxygen pressure regulating device (100) is disclosed. The device (100) comprises a housing (102) including an inlet port (104) and an outlet port (106), the housing (102) including: a spring unit (112) including a plate (116) placed in fluid communication with the inlet port (104), the plate (116) being configured to be moved when impinged upon by an oxygen stream at a first pressure received through the inlet port (104); a bellows arrangement (118); and a switch (146) configured to be activated to open the outlet port (106) for releasing the oxygen stream through the outlet port (106). Also disclosed is a system comprising the oxygen pressure regulating device (100), a laminar flow element and a second conduit.

11 Claims, 2 Drawing Sheets

OXYGEN PRESSURE REGULATING DEVICE AND SYSTEM

TECHNICAL FIELD

The present disclosure relates to respiratory therapy devices in general. More particularly, the present disclosure relates to an oxygen pressure regulating device which regulates the pressure of oxygen being delivered to a subject, e.g., a human subject.

BACKGROUND

Respiratory therapy devices and instruments generally provide oxygen at a pressure and volume that is suitable for the treatment of pulmonary ailments and diseases. Currently, devices such as oxygen cylinders, ventilators, oxygen concentrators, and direct oxygen supply in hospitals, are used to provide patients a positive oxygen pressure as part of the therapy. However, the pressure at which oxygen is supplied is often variable and, in most cases, the oxygen is supplied at a pressure different (e.g., higher pressure) than what is required for breathing. This causes a substantial wastage of oxygen, for instance, an oxygen cylinder typically loses around 5-10% due to inadequate or variable output oxygen pressure.

DETAILED DESCRIPTION

Figure 1:
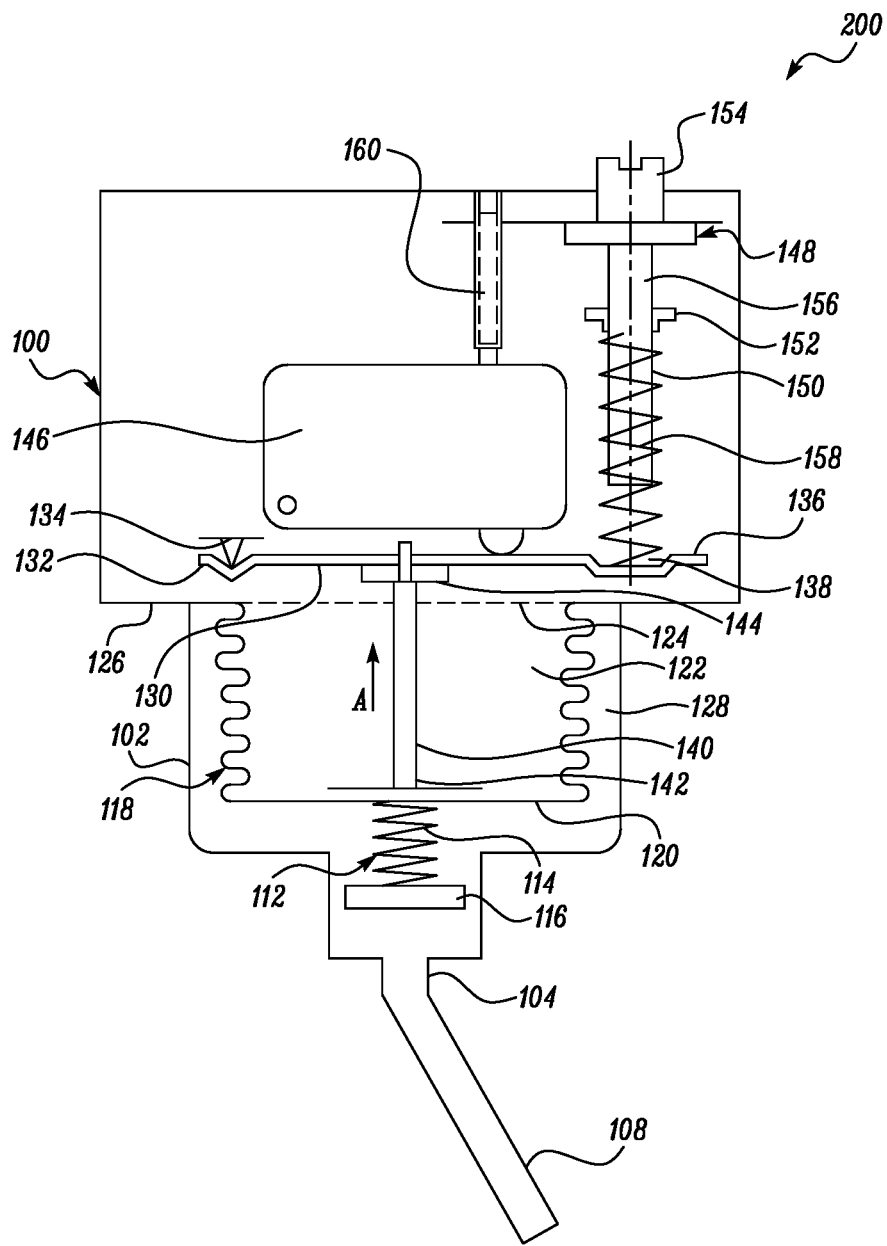
FIG. 1 is a schematic view illustrating an interior configuration of components of an oxygen pressure regulating device (100), in accordance with one or more aspects of the present disclosure.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates. Generally, corresponding reference numbers may be used throughout the drawings to refer to the same or corresponding parts, e.g., 1, 1', 1", 101 and 201 could refer to comparable components used in the same and/or different depicted embodiments.

It will be understood by those skilled in the art that the foregoing general description and the following detailed description are explanatory of the invention and are not intended to be restrictive thereof.

The terms "a," "an,", and "the" are used to refer to "one or more" (i.e. to at least one) of the grammatical object of the article.

Reference throughout this specification to "an aspect", "another aspect" or similar language means that a particular feature, structure, or characteristic described in connection with the embodiment is included in at least one embodiment of the present invention. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion and are not intended to be construed as "consists of only", such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Likewise, the terms "having" and "including" and their grammatical variants are intended to be non-limiting, such that recitations of said items in a list is not to the exclusion of other items that can be substituted or added to the listed items.

In an embodiment of the present disclosure, a system (200) is provided comprising an oxygen pressure regulating device (100) in fluid communication with an oxygen source by means of a first conduit (108) which is connected to an inlet port (104) of the oxygen pressure regulating device (100). A laminar flow element (202), which may be in fluid communication with the oxygen pressure regulating device (100) by means of a second conduit (110), is connected to an outlet port (106) by way of the second conduit (110). In other words, the second conduit (110) facilitates a supply of a laminar oxygen flow to the laminar flow element (202) from the outlet port (106). The laminar flow element (202) supplies a laminar oxygen flow at the second pressure to a subject e.g., a human being, by means of an outlet (not shown).

Figure 2:
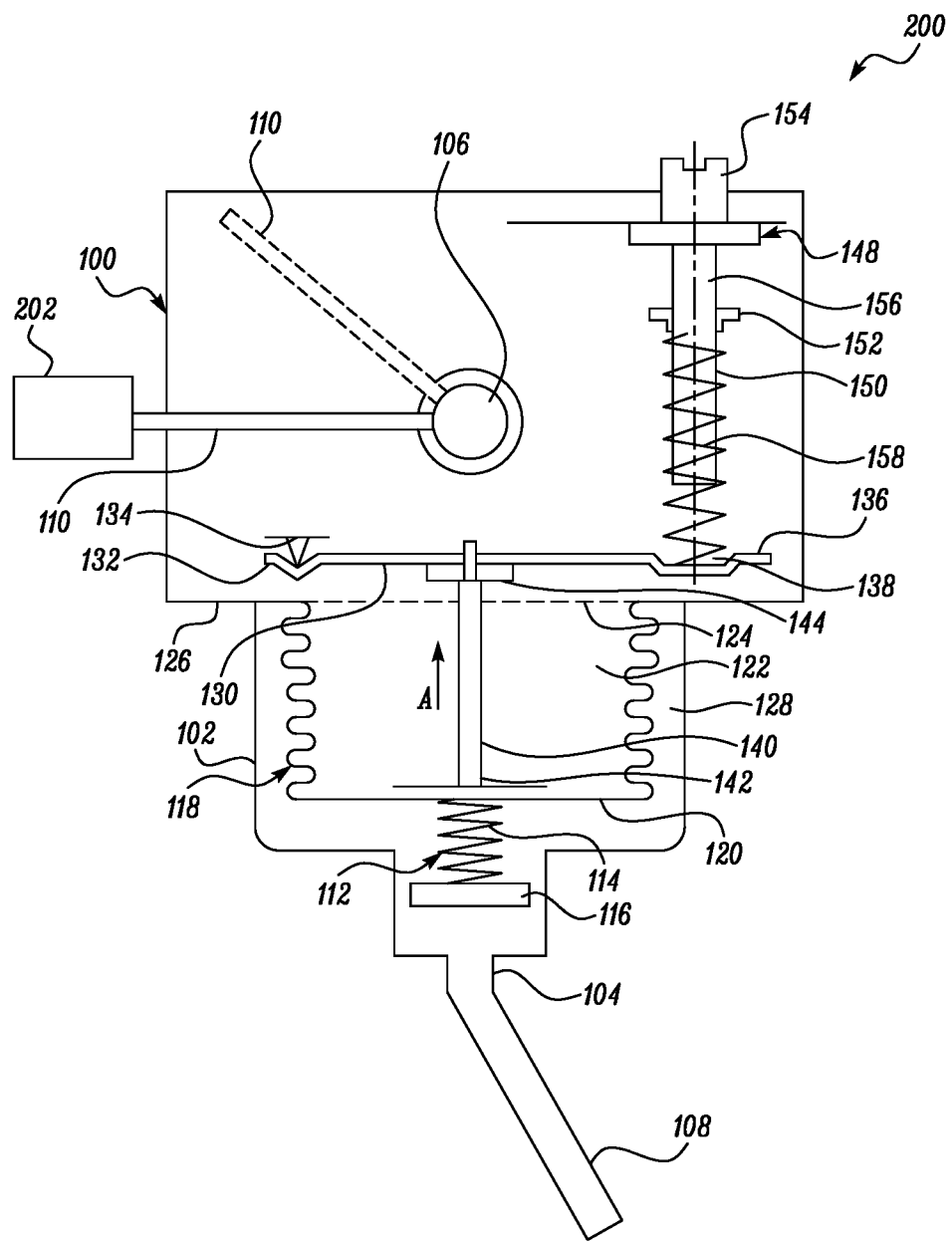
FIG. 2 is a schematic view illustrating the system (200) and the interior configuration of the device (100) with one or more of the components removed, in accordance with one or more aspects of the present disclosure.

Referring to FIGS. 1 and 2, the oxygen pressure regulating device (100) is illustrated. The device (100) is applied to regulate the pressure of a first oxygen stream supplied from an oxygen source such an oxygen cylinder, a piped oxygen supply, and manifolds. As an example, the device (100) comprises a housing (102) with an inlet port (104) configured to be in fluid communication with the oxygen supply by means of a first conduit (108). Further, the device (100) includes an outlet port (106), which supplies the oxygen stream at a second pressure to a subject by means of a second conduit (110). The housing (102) encloses pressure balancing components of the device (100) which include a spring unit (112), a bellows arrangement (118), a plate (130) pivoted on a pin (140), and a programmable switch (146).

The housing (102) may also include a calibration unit (148) for calibrating a state of an assembly of the spring unit (112) and the bellows arrangement (118). The components of the calibration unit (148) may include a calibration screw (150) which may include a head portion (154) and a shank portion (156), and a calibration spring (158).

The inlet port (104) as illustrated in FIG. 1 may extend outward from a wall of the housing (102) and may be in fluid communication with an oxygen source by means of the first conduit (108). The first conduit (108) may be fastened to the inlet port (104) by means of any suitable mechanism, e.g., a threadable mechanism. In one embodiment, the first conduit (108) may be fastened to the inlet port (104) to form an air-tight seal. Alternatively, it is contemplated that the first conduit (108) may be fastened to the inlet port (104) by means of one or more fasteners (not shown).

The spring unit (112) is disposed facing the inlet port (104) within the housing (102). The spring unit (112) includes a spring (114) and a plate (116). One end of the spring (114) is coupled to the plate (116) and the plate (116) is positioned such that it is pivoted on the spring (114) and directly faces the oxygen stream entering the inlet port (104).

In an embodiment, the plate (116) is a pressure sensor. The pressure sensor may be of any type including gauge, absolute, or differential sensors.

The bellows arrangement (118) is biased with respect to the spring (114) of the spring unit (112). The bellows arrangement (118) defines a first end (120) coupled to the spring unit (112) and/or in contact with the spring (114) of the spring unit (112). The first end (120) of the bellows arrangement (118) is followed by a cylindrical portion (122) that is able to compress and expand axially thereby allowing axial movement. A second end (124) of the bellows arrangement (118) is fixed to an edge (126) of the housing (102) by suitable means, e.g., by use of adhesives between the second end (124) and the edge (126) of the housing (102), or by welding the second end (124) of the bellows arrangement to the edge (126), or by pivoting the second end (124) of the bellows arrangement (118) in place by means of screws.

The circumference of the bellows arrangement (118) defines a channel (128) along the housing (102) which allows for the passage of the oxygen stream into the device (100).

The plate (130) is disposed along the second end (124) of the bellows arrangement (118) and is fixed at its one end (132) by means of a pivot pin (134). The plate (130) is movable along the pivot (134) in an axial direction (A) and is configured to contact the switch (146) upon the compression of the bellows arrangement (118). The plate (130) may also include a concavity (138) at the other end (136) of the plate (130) to receive the calibration spring (158) of the calibration unit (148).

The movement of the plate (130) is facilitated by the pin (140). The first end (142) of the pin (140) maybe coupled or may be in contact with the first end (120) of the bellows arrangement (118), while the second end (144) of the pin (140) may be coupled or in contact with the plate (130). The pin (140) maybe placed within a hollow interior of the cylindrical portion (122) of the bellows arrangement (118).

In an alternate embodiment, the pin (140) is omitted, and the bellows arrangement (118) may be directly coupled with the plate (130) such that the plate (130) may be deflected to contact the switch (146) upon the movement of the bellows arrangement (118).

The switch (146) maybe any commercially available electrical switch and maybe configured to be activated to open the outlet port (106), e.g., by way of swinging open a gate (not shown) at the outlet port (106). The switch (146) maybe coupled to a base wall of the housing (102) by means of an adhesive. Alternatively, the switch (146) maybe positioned in place by means of at least one screw to the base wall of the housing (102).

The device (100) may include a calibration unit (148) for calibrating a state of an assembly of the spring unit (112) and the bellows arrangement (118) such that a second pressure of the oxygen stream released from the outlet port (106) is different from the first pressure of the oxygen stream received from the inlet port (104). The calibration unit (148) may include a calibration screw (150) which may include a head portion (154) and a shank portion (156). The shank portion (156) may extend from the head portion (154) and may include threads that may engage with comporting threads (not shown) structured and arranged within a body of the housing (102). In an assembled state of the oxygen pressure regulating device (100), the head portion (154) may be disposed outwards of the housing (102), and the shank portion (156) may be disposed, at least in part, within the housing (102). A torque in a first direction (e.g., clockwise direction) may be provided to the head portion (154) to cause the calibration screw (150) to be moved (e.g., linearly) inwardly into the housing (102). A torque in a second direction (e.g., counterclockwise direction) may be provided to the head portion (154) to cause the calibration screw (150) to be moved (e.g., linearly) outwardly away from the housing (102).

A calibration spring (158) may be disposed around the shank portion (156). One end of the calibration spring (158) may abut a tip (152) defined in the shank portion (156). The other end of the calibration spring (156) may abut the end (136) of the plate (130) or alternatively, the concavity (138) at the end (136) of the plate (130). Upon turning the adjustment head (120) the movement of the calibration screw (150) causes the calibration spring (158) to compress and move (e.g., deflect) the plate (130). This arrangement may counterbalance any pressure exerted by the spring unit (112), bellows arrangement (118), and pin (140) on the plate (130), when the oxygen stream enters through the inlet (104) at the first pressure.

In an alternate embodiment, the calibration screw (150) is disposed above the switch (146). The calibration screw (150) may be adjusted such that the calibration spring (158) is compressed against the switch (146) thereby counterbalancing the pressure exerted by the spring unit (112), bellows arrangement (118), and pin (140), when the oxygen stream enters through the inlet port (104) at the first pressure.

In an embodiment, the calibration screw (150) may be adjusted to set the state of the assembly of the spring unit (112) and the bellows arrangement (118) such that the second pressure of the oxygen stream released from the outlet port (106) is in the range of 40%-100% of the first pressure of the oxygen stream, which is received at the inlet port (104). In another embodiment, the calibration screw (150) is adjusted to set the state of the assembly of the spring unit (112) and the bellows arrangement (118) such that the second pressure of the oxygen stream at the outlet port (106) is at 50% of the first pressure of the oxygen stream which is received at the inlet port (104). In a further embodiment, the assembly of the spring unit (112) and the bellows arrangement (118) is set such that the second pressure attains a value that is suitable to be supplied to the subject's lungs.

Also provided in the calibration unit (148) is a switch adjustment means (160). The switch adjustment means (160) may be used to position the switch (146) with respect to the plate (130) to ensure that the plate (130) abuts the switch (146) only when the first pressure of the oxygen supply is applied.

In an embodiment, a laminar flow element (202) may be fluidly coupled to the outlet port (106) or to the second conduit (110). The laminar flow element (202) may be configured to convert any turbulent flow of the oxygen stream released from the outlet port (106) to a laminar oxygen flow, suitable to be supplied to the subject.

INDUSTRIAL APPLICATION

The present disclosure relates to an oxygen pressure regulating device (100). The oxygen pressure regulating device (100) includes a housing (102) including an inlet port (104) and an outlet port (106), the housing (102) including:

a spring unit (112) including a plate (116) placed in fluid communication with the inlet port (104), the plate (116) is configured to be moved when impinged upon by the oxygen stream at the first pressure received through the inlet port (104);

a bellows arrangement (118) biased with respect to the spring unit (112);

a pin (140) coupled to the bellows arrangement (118), the pin (140) configured to move as the oxygen stream with the first pressure impinges on the plate (116) and moves the plate (130); and a switch (146) configured to be activated based on the movement of the pin (140) to open the outlet port (106) for releasing the oxygen stream through the outlet port (106), wherein the oxygen stream released through the outlet port (106) is released at a second pressure different from the first pressure.

During operation of the device (100), the oxygen stream enters the housing (102) through the inlet port (104) at a first pressure and impinges upon the plate (116) of the spring unit (112). The spring unit (112) is thereby compressed and accordingly causes the movement of the bellows arrangement (118). The movement of the bellows arrangement (118) absorbs the pressure exerted by the oxygen stream and provides passage to the oxygen stream entering from the inlet port (104) to flow annularly along the channel (128) defined between the bellows arrangement (118) and the housing (102). The spring unit (112) or the spring (114) of the spring unit (112) and the bellows arrangement (118) may correspondingly define inherent resistance values. As soon as the first pressure overcomes the resistance offered by the assembly of the spring unit (112) and the bellows arrangement (118), the bellows arrangement (118) pushes and displaces the pin (140) (e.g., axially) such that the pin (140) abuts and pushes against the plate (130), which in turn contacts and/or energizes the switch (146). The switch (146) then activates and moves the gate to an open state to open the outlet port (106) for a release of the oxygen stream from the outlet port (106) into the second conduit (110), for instance. In other words, as the outlet port (106) opens, the outlet port (106) allows the oxygen stream collected within the housing (102) to be discharged or released into the second conduit (110) at the reduced, second pressure of the oxygen stream. In some embodiments, the oxygen stream is released from the outlet port (106) at the second pressure, which may be equivalent to 50% of the first pressure of the oxygen stream received into the housing (102) from the inlet port (104).

The present oxygen pressure regulating device (100) is able to help save oxygen consumption (e.g., for noninvasive treatment) by up to 50%. Further, it is able to increase the SpO2 (i.e., oxygen saturation) levels by 4% in a subject receiving oxygen through a respiratory therapy device. This is due to the ability of the present device (100) to supply oxygen at a comfortable and appropriate pressure thus ensuring high oxygen consumption by the subject. The device (100) is also portable, does not require any electricity, and is easy to install, therefore enabling its widespread use in a variety of environments including hospitals, clinics, and homes.

We claim:

1. An oxygen pressure regulating device (100), comprising:
    a housing (102) including an inlet port (104) and an outlet port (106), the housing (102) including:
    a spring unit (112) including a plate (116) placed in fluid communication with the inlet port (104), the plate (116) directly facing an oxygen stream entering the inlet port (104) and being configured to be moved when impinged upon by the an oxygen stream at a first pressure received through the inlet port (104);
    a bellows arrangement (118) coupled to the spring unit (112) and biased with respect to the spring unit (112);
    a pin (140) coupled to the bellows arrangement (118), the pin (140) configured to move as the oxygen stream with the first pressure impinges on the plate (116) and moves the plate (116); and
    a switch (146) configured to be activated based on the movement of the pin (140) to open the outlet port (106) for releasing the oxygen stream through the outlet port (106), wherein the oxygen stream released through the outlet port (106) is released at a second pressure different from the first pressure when the first pressure overcomes a resistance offered by an assembly of the spring unit (112) and the bellows arrangement (118).

2. The device (100) as claimed in claim 1, wherein the spring unit (112) includes a spring (114) defining an end that is coupled to the plate (116).

3. The device (100) as claimed in claim 2, wherein the plate (116) is pivoted on the spring (114).

4. The device as claimed in claim 2, wherein the bellows arrangement defines a first end coupled to or in contact with the spring and a second end which is fixed to an edge of the housing.

5. The device (100) as claimed in claim 4, wherein the first end (120) of the bellows arrangement (118) is followed by a cylindrical portion (122) that is configured to compress and expand axially thereby allowing axial movement.

6. The device (100) as claimed in claim 1, further comprising a second plate (130) coupled with the pin (140), wherein the second plate (130) is movable along a pivot (134) in an axial direction (A) and is configured to contact the switch (146) upon the compression of the bellows arrangement (118).

7. The device (100) as claimed in claim 1, wherein the device comprises a calibration unit (148) for calibrating a state of an assembly of the spring unit (112) and the bellows arrangement (118).

8. The device (100) as claimed in claim 7, wherein the calibration unit (148) includes a calibration screw (150) comprising a head portion (154) and a shank portion (156) and configured to be adjusted to counterbalance a pressure or resistance exerted by the spring unit (112), the bellows arrangement (118), and the pin (140).

9. The device (100) as claimed in claim 1, wherein the second pressure of the oxygen stream is released from the outlet port (106) at 40%-100% of the first pressure of the oxygen stream which is received at the inlet port (104).

10. A system (200), comprising:
    the oxygen pressure regulating device (100) as claimed in claim 1, the oxygen pressure regulating device (100) in fluid communication with an oxygen source by means of a first conduit (108) which is connected to the inlet port (104) of the oxygen pressure regulating device (100); and
    a laminar flow element (202) in fluid communication with the oxygen pressure regulating device (100) by means of a second conduit (110) which facilitates a supply of a laminar oxygen flow to the laminar flow element (202) from the outlet port (106).

11. An oxygen pressure regulating device (100), comprising:
    a housing (102) including an inlet port (104) and an outlet port (106), the housing (102) including:

a spring unit (112) including a plate (116) placed in fluid communication with the inlet port (104), the plate (116) being configured to be moved when impinged upon by the oxygen stream at a first pressure received through the inlet port (104);

a bellows arrangement (118) coupled to the spring unit (112) and biased with respect to the spring unit (112);

a pin (140) coupled to the bellows arrangement (118), the pin (140) configured to move as the oxygen stream with the first pressure impinges on the plate (116) and moves the plate (116);

a second plate (130) coupled with the pin (140), wherein the second plate (130) is moveable along a pivot (134) in an axial direction (A) and is configured to contact a switch (146) upon the compression of the bellows arrangement (118); and the switch (146) configured to be activated based on the movement of the pin (140) to open the outlet port (106) for releasing the oxygen stream through the outlet port (106), wherein the oxygen stream released through the outlet port (106) is released at a second pressure different from the first pressure when the first pressure overcomes a resistance offered by an assembly of the spring unit (112) and the bellows arrangement (118).

* * * * *